United States Patent [19]

Sakamoto et al.

[11] 4,136,191
[45] Jan. 23, 1979

[54] COMPOSITION AND METHOD FOR TREATING OR PREVENTING FOWL COCCIDIOSIS

[75] Inventors: Koji Sakamoto; Takeshi Asano, both of Takasaki; Kazuo Mizuochi, Tokyo; Kanemichi Sasaki, Koshigaya; Kouji Hasegawa, Omiya, all of Japan

[73] Assignees: Nippon Kayaku Kabushiki Kaisha; Chugai Seiyaku Kabushiki Kaisha, both of Tokyo, Japan

[21] Appl. No.: 870,487

[22] Filed: Jan. 18, 1978

[30] Foreign Application Priority Data

Jan. 21, 1977 [JP] Japan .................................... 52-4979

[51] Int. Cl.² ............................................ A61K 31/365
[52] U.S. Cl. .................................................... 424/279
[58] Field of Search .......................................... 424/279

[56] References Cited

U.S. PATENT DOCUMENTS 3,777,023  12/1973  Sagawa et al. ........................ 424/279

Primary Examiner—Sam Rosen
Attorney, Agent, or Firm—Schuyler, Birch, Swindler, McKie & Beckett

[57] ABSTRACT

A composition and method for treating or preventing fowl coccidiosis, said composition comprising one or more of the macrotetrolide antibiotic substances represented by the general formula

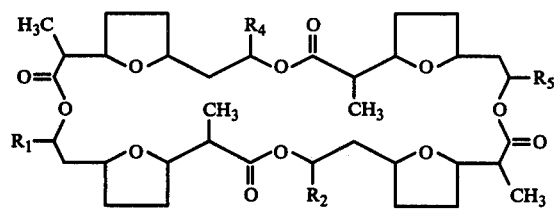

wherein $R_1$, $R_2$, $R_3$ and $R_4$ each represents methyl or ethyl group, and a physiologically acceptable carrier.

10 Claims, No Drawings

COMPOSITION AND METHOD FOR TREATING OR PREVENTING FOWL COCCIDIOSIS

This invention relates to a composition and method for preventing and treating coccidiosis of fowls and, more particularly, it relates to a composition and method for preventing and treating coccidiosis of fowls, said composition comprising one or more of the macrotetrolide antibiotic substances represented by the general formula (I)

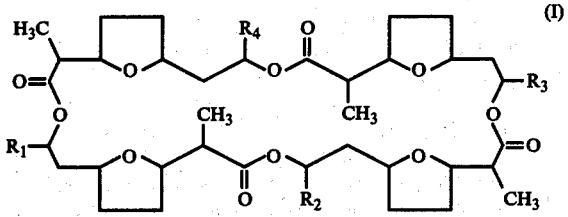

(I)

wherein $R_1$, $R_2$, $R_3$ and $R_4$ each represents a methyl group or ethyl group and a physiologically acceptable carrier.

Fowl coccidiosis is an infectious disease accompanying gastrointestinal disturbance and malnutrition caused by the oocyst of coccidia swallowed by the fowl. Fowls such as chicken, duck, quail and turkey are known to be susceptible of coccidiosis. Of the above-noted fowls, especially the chickens are bred collectively in a limited space and, hence, once the coccidiosis outbreaks it is communicated to the whole mass of chickens, leading generally to 100% mortality. Even if a certain number of chickens survived, they have to be disposed of as discarded, resulting in a large economical loss.

Conventional treatment of the coccidiosis has consisted in administration of antithiamines, quinoline derivatives and sulfonamides. However, such preparations cannot be called satisfactory drugs, because problems have recently been aroused concerning their efficacy, safety to the animals under treatment, and the emergence of strains resistant to said preparations.

The present inventors carried out various experiments on prophylactic and therapeutic agents for coccidiosis and, as a result, found that the macrotetrolide and antibiotic substance represented by the above-said general formula (I) exhibits, as a prophylactic and therapeutic agent, a distinguished effect upon fowl caccidiosis. Based on this finding, the present invention has been accomplished.

An object of the present invention is to provide a composition and method for treating or preventing fowl coccidiosis.

Other objects and advantages of the present invention will be apparent from the following descriptions.

The antibiotic substances represented by the general formula (I) and used in this invention are known compounds which were described in, for example, Helvetica Chimica Acta, 38, 1445-1448 (1955); 45, 129-138 (1962); 45, 620-630 (1962). These compounds are produced by cultivating Streptomyces aureus in nutritive media (Japanese Patent Publication No. 45,597/74) and are known as insecticides and miticides (U.S. Pat. No. 3,777,023).

Depending upon the method of production and the procedure of purification, the above antibiotic substances are sometimes found in the form of various stereoisomers of the same chemical formula but of the slightly different physical and chemical properties. In the present invention, all of these stereoisomers can be used without any discrimination.

Typical compounds represented by the general formula (I) are as shown in Table 1.

Table 1

| | Compound No. | | | | |
|---|---|---|---|---|---|
| | 1 | 2 | 3 | 4 | 5 |
| Name | Nonactin | Monactin | Dinactin | Trinactin | Tetranactin |
| $R_1$ | $CH_3$ | $C_2H_5$ | $C_2H_5$ | $C_2H_5$ | $C_2H_5$ |
| $R_2$ | $CH_3$ | $CH_3$ | $C_2H_5$ | $C_2H_5$ | $C_2H_5$ |
| $R_3$ | $CH_3$ | $CH_3$ | $CH_3$ | $C_2H_5$ | $C_2H_5$ |
| $R_4$ | $CH_3$ | $CH_3$ | $CH_3$ | $CH_3$ | $C_2H_5$ |
| MP (° C) | 148 – 149 | 63 – 64 | 73 – 74 | 79 – 80 | 105 – 106 |

The above compounds are of extremely low toxicity, the acute oral toxicity ($LD_{50}$) being >25,000 mg/kg for mouse, >2,500 mg/kg for rat and >2,000 mg/kg for quail.

The macrotetrolide antibiotic substance obtained by cultivation of Streptomyces aureus is generally a mixture comprising dinactin, trinactin and tetranactin as major components. Such a mixture is called polynactin complex (generic name).

The composition of this invention for the prophylactic and therapeutic treatment of coccidiosis is prepared by blending the macrotetrolide antibiotic substance represented by the general formula (I) with a physiologically harmless solid or liquid carrier and contains 10 ppm or more, preferably 1,000 ppm or more of the active ingredients.

Examples of the solid carriers for use in preparing the composition include wheat meal, soybean meal, defatted rice bran, corn starch, calcium carbonate, talc, kaolin, chalk and diatomaceous earth. Examples of the liquid carriers are water and physiological sodium chloride solution. If necessary, adjuvants or additives such as emulsifiers, dispersants, suspending agents and wetting agents may be additionally used.

In preventing or treating the coccidiosis, it is sufficient to administer continuously to the fowl 0.5 to 100 mg/kg of fowl's weight in terms of active ingredient of the present composition. In actual practice, it is recommendable to raise the fowl on a feed incorporated with the present composition in a proportion of 10 to 1,000 ppm in terms of active ingredient. It is not objectionable to add to the feed other agents such as conventional anti-coccidiosis agents or growth stimulating agents for fowls.

The efficacy of the present composition in the prophylactic and therapeutic treatment of coccidiosis is illustrated below with reference to Examples.

EXPERIMENTAL EXAMPLE 1

(1) Procedure

Female broiler chicks were submitted to the experiment. Concentrations of a polynactin complex (containing 10% of dinactin, 40% of trinactin and 50% of tetranactin) in the feed were 10, 50, 100, 250, 500, 1,000 and 2,000 ppm. A feed without the addition of polynactin complex was used as control. After breeding the day-old chicks for 5 days on a base feed containing no polynactin complex, the 6-day old chicks were divided in groups and bred in separate cages on different feeds under test containing the polynactin complex in different concentrations as given above. When the chicks became 8-day old, each was orally administered with 2 × $10^4$ pieces of the oocyst of Eimeria tenella. After 8 days from the administration of oocyst, the chicks were autopsied to estimate the extent of progress of coccidiosis by inspecting the pathological change in the cecum. The pathological change was rated on the basis of the following criteria for 5 rating classes:

−: The cecum is perfectly normal.

+: The cecum is normal in shape; the contents are slightly fluid and yellowish in color; the mucosa is locally swollen a little and whitish in color.

++: The cecum is nearly normal in shape; swelling of the mucosa is visible all over the wall; no bleeding is found in the contents; the mucin is tinged with yellow and faded in color; a small number of white spots, necrosis spots and hemorrhagic spots are visible within the mucosa.

+++: Atrophy and deformation of the cecum are distinctive, the cecum becoming slightly larger in length than the rectum; generally, normal contents are entirely absent and filled with coagulated blood or a greyish white chesse-like degenerated matter; the cecum markedly increases in wall thickness and becomes brittle; petechiae still remains in some cases; pathological change extends to the basal end of cecum but not to the rectum.

++++: Atrophy and deformation of the cecum are distinctive, becoming sausage-like in shape; the length becomes the same as or shorter than that of rectum; pathological change extends to the upper one-third or one-fourth of the rectum; other changes are the same as in the case of +++.

(2) Results

As shown in Table 2, the pathological change in the cecum of the chicken groups administered with the polynactin complex was very slight, indicating clearly the anti-coccidiosis activity of the present composition.

Table 2

| Concentration of polynactin complex added, ppm | Number of chicks | \++++ | +++ | ++ | + | − |
|---|---|---|---|---|---|---|
| 2000 | 5 | 0 | 0 | 0 | 1 | 4 |
| 1000 | 5 | 0 | 0 | 0 | 1 | 4 |
| 500 | 5 | 0 | 0 | 0 | 2 | 3 |
| 250 | 5 | 0 | 0 | 0 | 3 | 2 |
| 100 | 5 | 0 | 0 | 0 | 4 | 1 |
| 50 | 5 | 0 | 0 | 1 | 3 | 1 |
| 10 | 5 | 0 | 0 | 4 | 1 | 0 |
| 0 | 5 | 4 | 1 | 0 | 0 | 0 |

EXPERIMENTAL EXAMPLE 2

(1) Procedure

Female broiler chicks were submitted to the experiment. Concentrations of a polynactin complex (containing 3% of dinactin, 7% of trinactin and 90% of tetranactin) in the feed were 10, 50, 100, 250, 500, 1,000 and 2,000 ppm. A feed without the addition of the polynactin complex was used as control. After breeding the day-old chicks for 5 days on a base feed containing no polynactin complex, the 6-day old chicks were divided in groups and bred in separate cages on different feeds under test containing the polynactin complex in different concentrations as given above. When the chicks became 8-day old, each was orally administered with 2 × $10^4$ pieces of the oocyst of *Eimeria necatrix*. After 8 days from the administration of oocyst, the chicks were autopsied to estimate the extent of progress of coccidiosis by inspecting the pathological change in the small intestine.

The pathological change in small intestine was rated on the basis of the following criteria for 5 classes of rating:

−: The small intestine is perfectly normal.

+: The small intestine is normal; a small number of tiny necrosis spots or hemorrhagic spots are visible in the mucosa at the middle part of the small intestine.

++: The small intestine is normal in shape; spotty white necrosis foci and hemorrhagic spots are scattered within the mucosa at the middle part of small intestine; a small amount of mucin and blood appears in the intestinal contents.

+++: At the middle part, the small intestine dilates and the mucous wall becomes thicker and shows innumerable hemorrhagic spots; the hemorrhagic spots are very few in the duodenum and lower part of the small intestine; a large amount of mucin and hemorrhage are noticeable in the intestine contents; there is scarcely any change in the cecum and rectum.

++++: A large number of hemorrhagic spots are visible also in the duodenum and the lower part of small intestine; other pathological changes are the same as with the rating +++.

(2) Results

As shown in Table 3, the administration of a polynactin complex lessened the pathological change due to infection of *Eimeria necatrix* in the small intestine, indicating the anticoccidiosis activity of the present composition.

Table 3

| Concentration of polynactin complex added ppm | Number of chicks | ++++ | +++ | ++ | + | − |
|---|---|---|---|---|---|---|
| 2000 | 5 | 0 | 0 | 0 | 0 | 5 |
| 1000 | 5 | 0 | 0 | 0 | 1 | 4 |
| 500 | 5 | 0 | 0 | 0 | 2 | 3 |
| 250 | 5 | 0 | 0 | 0 | 2 | 3 |
| 100 | 5 | 0 | 0 | 0 | 4 | 1 |
| 50 | 5 | 0 | 0 | 1 | 3 | 1 |
| 10 | 5 | 0 | 1 | 3 | 1 | 0 |
| 0 | 5 | 4 | 1 | 0 | 0 | 0 |

EXPERIMENTAL EXAMPLE 3

(1) Procedure

Female broiler chicks were submitted to the experiment. Concentrations of a polynactin complex (containing 3% of dinactin, 7% of trinactin and 90% of tetranactin) in the feed were 10, 50, 100, 250, 500, 1,000 and 2,000 ppm. A feed without the addition of the polynactin complex was used as control. After breeding the day-old chicks for 5 days on a base feed containing no polynactin complex, the 6-day old chicks were divided in groups and bred thenceforth in separate testing cages on different feeds under test containing the polynactin complex in different concentrations as given above. When the chicks became 8-day old, each was orally administered with 4 × $10^4$ pieces of oocyst of *Eimeria acervulina*. After 7 days from the administration of oocyst, the chicks were autopsied to estimate the extent of progress of coccidiosis by inspecting the pathological change in the small intestine. The rating of the pathological change was carried out of the basis of the same criteria as in Experimental Example 2.

(2) Results

As shown in Table 4, the polynactin complex showed an evident anticoccidiosis activity against *Eimeria acervulina*.

Table 4

| Concentration of polynactin complex added ppm | Number of chicks | Number of cases for each rating of pathological change in small intestine | | | | |
|---|---|---|---|---|---|---|
| | | ++++ | +++ | ++ | + | − |
| 2000 | 5 | 0 | 0 | 0 | 0 | 5 |
| 1000 | 5 | 0 | 0 | 0 | 0 | 5 |
| 500 | 5 | 0 | 0 | 0 | 2 | 3 |
| 250 | 5 | 0 | 0 | 0 | 1 | 4 |
| 100 | 5 | 0 | 0 | 0 | 3 | 2 |
| 50 | 5 | 0 | 0 | 0 | 4 | 1 |
| 10 | 5 | 0 | 0 | 2 | 3 | 0 |
| 0 | 5 | 3 | 2 | 0 | 0 | 0 |

EXPERIMENTAL EXAMPLE 4

(1) Procedure

Female broiler chicks were submitted to the experiment. The feed was incorporated with nonactin, monactin, dinactin, trinactin or tetranactin in a concentration of 10, 50, 100, 250, 500 or 1,000 ppm. A feed containing none of the above chemicals was used as control. After breeding the day-old chickens for 5 days on a base feed containing no chemical, the 6-day old chicks were divided in groups and bred thenceforth in separate testing cages on different feeds under test containing the above-noted chemicals in different concentrations as given above. When the chicks became 8-day old, each was orally administered with $2 \times 10^4$ pieces of oocyst of *Eimeria tenella*. After 8 days from the administration of oocyst, the chicks were autopsied to estimate the extent of progress of coccidiosis by inspecting the pathological change in the cecum. The rating of the pathological change was carried out on the basis of the same criteria as in Experimental Example 1.

(2) Results

As shown in Table 5, the coccidiosis developed in the groups of chicks bred on the feeds incorporated with nonactin, monoactin, dinactin, trinactin or tetranactin was very mild, as compared with the control, indicating an evident anticoccidiosis activity of said chemicals.

Table 5

| Name of compound | Amount added, ppm | Number of chicks | Number of cases for each rating of pathological change in cecum | | | | |
|---|---|---|---|---|---|---|---|
| | | | ++++ | +++ | ++ | + | − |
| Nonactin | 1000 | 5 | 0 | 0 | 0 | 1 | 4 |
| | 100 | 5 | 0 | 0 | 0 | 3 | 2 |
| | 10 | 5 | 0 | 0 | 2 | 3 | 0 |
| Monactin | 1000 | 5 | 0 | 0 | 0 | 1 | 4 |
| | 100 | 5 | 0 | 0 | 0 | 4 | 1 |
| | 10 | 5 | 0 | 0 | 3 | 2 | 0 |
| Dinactin | 1000 | 5 | 0 | 0 | 0 | 1 | 4 |
| | 100 | 5 | 0 | 0 | 0 | 4 | 1 |
| | 10 | 5 | 0 | 0 | 3 | 2 | 0 |
| Trinactin | 1000 | 5 | 0 | 0 | 0 | 0 | 5 |
| | 100 | 5 | 0 | 0 | 0 | 2 | 3 |
| | 10 | 5 | 0 | 0 | 4 | 1 | 0 |
| Tetranactin | 1000 | 5 | 0 | 0 | 0 | 0 | 5 |
| | 100 | 5 | 0 | 0 | 0 | 1 | 4 |
| | 10 | 5 | 0 | 0 | 3 | 2 | 0 |
| Control | 0 | 5 | 4 | 1 | 0 | 0 | 0 |

What is claimed is:

1. A method for preventing or treating fowl coccidiosis, which comprises administering to the fowl an effective amount of an antibiotic substance of the macrotetrolide type.

2. A method for preventing or treating fowl coccidiosis according to claim 1, wherein the antibiotic substance of the macrotetrolide type is admixed with a feed and orally administered to the fowl.

3. A method for preventing or treating fowl coccidiosis according to claim 1, wherein the effective amount is 0.5 to 100mg/kg of fowl's weight.

4. A method for preventing or treating fowl coccidiosis according to claim 2, wherein 10 to 1000 ppm of the antibiotic substnce of the macrotetrolide type is admixed with the feed.

5. A method for preventing or treating fowl coccidiosis, which comprises administering to a fowl an effective amount of at least one antibiotic substance of the macrotetrolide type represented by the general formula

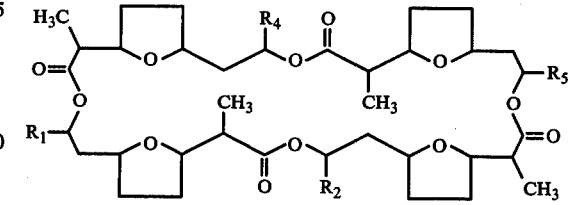

wherein $R_1$, $R_2$, $R_3$ and $R_4$ each represents a methyl or ethyl group.

6. A method for preventing or treating fowl coccidiosis according to claim 5, wherein at least one antibiotic substance of the macrotetrolide type admixed with a feed is orally administered to the fowl.

7. A method for preventing or treating fowl coccidiosis according to claim 5, wherein the antibiotic substance of the macrotetrolide type is selected from the group consisting of nonactin, monoactin, dinactin, trinactin and tetranactin.

8. A method for preventing or treating fowl coccidiosis according to claim 5, wherein the antibiotic substance of the macrotetrolide type is polynactin complex.

9. A method for preventing or treating fowl coccidiosis according to claim 5, wherein the effective amount is 0.5 to 100mg/kg fowl's weight.

10. A method for preventing or treating fowl coccidiosis according to claim 6, wherein 10 to 1000 ppm of at least one antibiotic substance of the macrotetrolide type is admixed with the feed.

* * * * *